United States Patent [19]

Seper et al.

[11] Patent Number: 5,322,954

[45] Date of Patent: Jun. 21, 1994

[54] SYNTHESIS OF 4-SUBSTITUTED PHTHALIC ANHYDRIDES

[75] Inventors: Karl W. Seper, Youngstown; Jeffrey S. Stults; Gary H. Olsen, both of Grand Island, all of N.Y.

[73] Assignee: Occidental Chemical Corporation, Niagara Falls, N.Y.

[21] Appl. No.: 68,042

[22] Filed: May 28, 1993

[51] Int. Cl.$^5$ ............................................. C07D 307/89
[52] U.S. Cl. ...................... 549/246; 560/80; 560/83; 560/86; 560/96; 562/480; 562/488
[58] Field of Search ................ 549/246; 560/80, 83, 560/86, 96; 562/480, 488

[56] References Cited

U.S. PATENT DOCUMENTS

| | | | |
|---|---|---|---|
| 4,978,760 | 12/1990 | Spohn | 549/246 |
| 5,003,088 | 3/1991 | Spohn et al. | 549/246 |
| 5,049,682 | 9/1991 | Tang et al. | 549/246 |
| 5,059,697 | 10/1991 | Fertel et al. | 549/246 |

OTHER PUBLICATIONS

Bergmann, J. Appl. Chem., 3, pp., 145–146 (1953).

*Primary Examiner*—Bernard Dentz
*Attorney, Agent, or Firm*—Wayne A. Jones; Richard D. Fuerle

[57] ABSTRACT

Disclosed is a method of making a 4-substituted phthalic anhydride. A halomaleic (including halofumaric anhydride (or the acid or ester thereof) is made by the reaction of-maleic anhydride with chlorine or bromine. The halomaleic anhydride is reacted with a conjugated diene to form a first cycloadduct having the formula

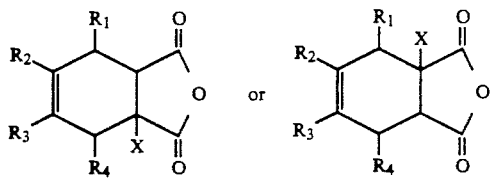 or The first cycloadduct is heated to eliminate HX and produce a second cycloadduct having the formula

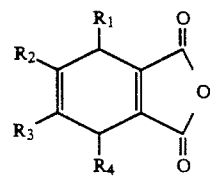

The second cyclo adduct is dehydrogenated to produce a 4substituted phthalic anhydride which has the formula

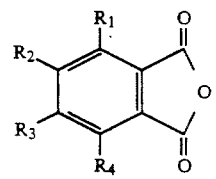

where $R_1$, $R_2$, and $R_4$ are preferably H and $R_3$ is preferably Cl or F.

17 Claims, No Drawings

SYNTHESIS OF 4-SUBSTITUTED PHTHALIC ANHYDRIDES

BACKGROUND OF THE INVENTION

This invention relates to a method of synthesizing 4-substituted phthalic anhydrides. In particular, it relates to a method of synthesizing 4-chlorophthalic anhydride (4-CPAN) from chloromaleic or bromomaleic anhydride, chloroprene, and an oxidizing agent such as air, oxygen, chlorine or bromine. Similarly, 4-fluorophthalic anhydride (4-FPAN) can be prepared from chloro or bromomaleic anhydride, hydrogen fluoride, chloroprene, and an oxidizing agent.

4-CPAN and 4-FPAN are valuable intermediates for the production of various specialty chemical products. While it is possible to prepare 4-CPAN by directly chlorinating phthalic anhydride, the principal products tend to contain di- and tri-chlorinated phthalic anhydrides as well as 3-chlorophthalic anhydride. While other methods exist for the formation of 4-CPAN by direct chlorination, these methods do not result in easily purified 4-CPAN. 4-FPAN can be prepared by the halogen exchange reaction of 4-CPAN with potassium fluoride.

In another approach (see U.S. Pat. Nos. 5,003,088 and 5,049,682) for preparing a 4-halophthalic anhydride, chloroprene is reacted with maleic anhydride to produce a substituted cyclohexene which is oxidized with a halogen such as chlorine or bromine. While this process successfully produces the desired 4-halophthalic anhydride, it requires the use of a halogen source such as chlorine or bromine in the aromatization reaction and produces hydrochloric or hydrobromic acid as a byproduct, as well as other byproducts, and it is difficult to separate the 4-halophthalic anhydride from the byproducts.

SUMMARY OF THE INVENTION

We have found that 4-substituted phthalic anhydrides can be made in high yield by reacting a particular type of diene with chloro- or bromomaleic anhydride. This results in the formation of novel cycloadducts. These cycloadducts can be easily oxidized with air or oxygen in the presence of activated carbon at relatively low temperatures to produce a 4-halo substituted phthalic anhydride. That this process would produce 4-halo substituted phthalic anhydrides in high yields was unexpected since chloromaleic anhydride was not known to undergo a cycloaddition reaction with the particular dienes used in the process of this invention. Also, it is surprising that intermediates formed in the process can be oxidized to 4-halo substituted phthalic anhydride using only air or oxygen in the presence of activated carbon at low temperatures, as one would normally expect more severe conditions to be required.

DESCRIPTION OF THE INVENTION

Halogenation Reaction

In the first step of the process of this invention, chlorine or bromine is reacted with a maleic compound having the structural formula

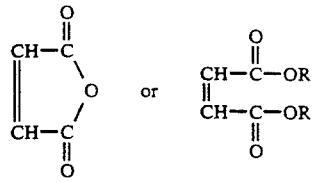

where each R is independently selected from H, alkyl to $C_{10}$ or aryl. (It should be understood that the term "maleic" is intended to include both the cis and trans, i.e., fumaric, isomers.) Preferably the maleic compound is maleic anhydride as that compound is commercially available and reacts readily. Esters remain esters through subsequent reactions and the ester product must be converted to an anhydride by hydrolysis followed by cyclization. Acids may convert to anhydrides during the aromatization reaction, or they can be converted by thermal or chemical methods which are well known to those skilled in the art.

The halogenation of the maleic compound proceeds readily at about 130° to about 170° C. The reaction is preferably performed in the presence of light, which lowers the temperature required for the reaction. A catalyst, such as aluminum trichloride, in an amount of about 6 to about 100 wt % (based on the weight of the maleic compound), can be used to accelerate the reaction and minimize the formation of dichloromaleic anhydride.

While maleic anhydride (and other maleic compounds) can be chlorinated in a solvent, it is preferable to carry out the reaction in the melt and bubble chlorine or bromine gas through it while following the reaction using gas chromatography (GC). The reaction is complete after several hours. The product is a mixture of monohalo maleic anhydride and dihalo maleic anhydride in a molar ratio of about 4:1. The mixture, suitable for the following chemical reactions, can be recovered by flash distillation at about 12 torr and about 140° C.

Monochloromaleic anhydride can be prepared according to procedures well-known in the published literature. See, for example, the citations on page 55 of "Organic Chlorine Compounds", by Huntress (John Wiley 1948), such as yon Auwers, Harres, *Ber.* 62 1686–1687 (1929) and Synerholm, *J. Amer. Chem. Soc.* 67, 345 and 1229–1230 (1945), herein incorporated by reference.

Cycloaddition Reaction

In the next step of the process of this invention, the halogenated maleic compound, which is a dienophile, is reacted with a conjugated diene that has the general formula

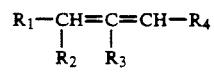

$R_1$, $R_2$, and $R_4$ are each independently selected from hydrogen, alkyl to $C_6$, aryl and halo, and $R_3$ is alkyl to $C_6$ or halo. Preferably, $R_2$ or $R_3$ or both are halo, preferably chlorine, bromine, or fluorine, as products made with those compounds are more valuable. It is contemplated that $R_2$ and $R_3$ can join together or that $R_1$ and $R_4$ can join together (i.e., cycloalkyl), such as in 1,3-cyclohexadiene. However, it is not contemplated that both $R_1$ and $R_2$ are joined together and $R_2$ and $R_3$ are joined together. Of the conjugated dienes within the scope of the above formula, the 1,3-dienes are preferred as they are more reactive.

Examples of suitable conjugated dienes include chloroprene, bromoprene, fluoroprene and isoprene. The preferred conjugated dienes are chloroprene and fluoroprene as those compounds are readily available and valuable products can be made from them.

The amount of conjugated diene used in the reaction can vary considerably. Key considerations in determining the relative amounts of diene to dienophile are ease of preparation of the diene, cost of the diene, ease of recovery of the diene, and stability of the diene. Typically, an approximately stoichiometric amount of diene is used based on the amount of halomaleic compound.

The cycloaddition reaction is performed in a liquid medium. If the conjugated diene is a liquid, the conjugated diene can be used as the liquid medium. A solvent may also be used in the reaction. Examples of suitable solvents include toluene, chlorobenzene, dichlorobenzenes, benzene, carbon tetrachloride, and chloroform. Chorobenzene is the preferred solvent because it does not interfere in subsequent reactions. Sufficient solvent is added to dissolve the reactants. Chloroprene itself, without a solvent, can be refluxed at about 60° C.

In this reaction, it is also preferable to include a free radical inhibitor to stabilize the conjugated diene and prevent it from polymerizing. Some conjugated dienes, such as chloroprene, are sold with free radical inhibitors already present. If desired, up to about 1 wt % of a free radical inhibitor such as butylated hydroxy toluene (BHT) or phenothiazine (PTZ) can be used.

The reaction proceeds at a temperature from about room temperature to about 120° C. It may desirable to use pressure at the higher temperatures. The reaction can be followed on gas chromatography (GC) and the termination of the reaction can also be noted when the conjugated diene no longer refluxes, which normally takes about 2 to about 24 hours.

The product of the cycloaddition reaction between the conjugated diene and halomaleic compound is a cycloadduct. The cycloadduct, a tetrahydrophthalic anhydride, is believed to be novel and has the general formula

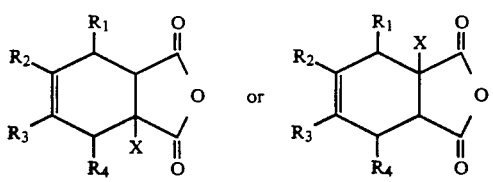

where X is chlorine or bromine. Unless it is desired to use a particular isomer, it is not necessary to isolate these isomers for the subsequent reactions.

The following cycloadducts, which are formed by the reaction of chloro- or bromo- maleic anhydride with fluoroprene or chloroprene, are believed to be novel and are particularly preferred:

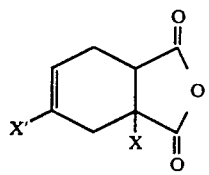

I.

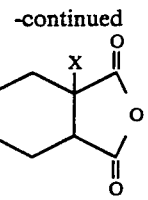

II.

where X' is fluorine or chlorine. Depending on the particular starting compounds, the ratio of cycloadduct I to cycloadduct II may vary from about 1:1 to about 3:1. If it is desired to isolate the novel compounds I and II, the temperature preferably should be kept below 100° C. during the cycloaddition reaction when X is chlorine to prevent the elimination of HCl, and at or below 60° C. when X is bromine to prevent the elimination of HBr, as that gives a higher yield. These compounds may be useful as intermediates in making plant growth inhibitors.

ELIMINATION REACTION

In the next step of the process of this invention, the cycloadducts formed in the previous step are heated to a temperature between about 60° and about 170° C., which results in the loss of HX. At lower temperatures the reactions are slow and higher temperatures may result in undesirable side products.

The resulting product, a dihydrophthalic anhydride, has the general formula:

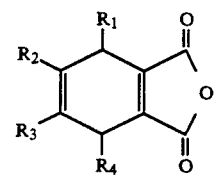

When the starting material is chloro- or bromo- maleic anhydride reacted with chloroprene or bromoprene the product has the formula

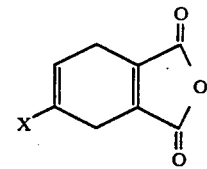

From nuclear magnetic resonance (NMR) it is believed that a small amount of

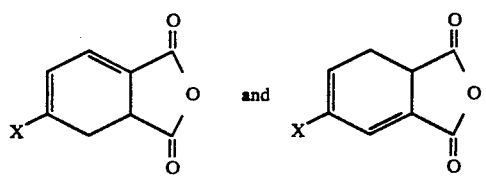

are also formed.

AROMATIZATION REACTION

The final reaction of the process of this invention is a dehydrogenation or aromatization reaction which removes two hydrogens from the product of the previous reaction, thereby forming an aromatic ring. This reaction can be performed using an aromatization agent, which can remove two hydrogens and form an aromatic ring at a temperature below 170° C. Examples of aromatization agents include oxygen, air, chlorine, bromine, N-bromosuccinimide (NBS), and N-chlorosuccinimide (NCS). The preferred aromatization agent is air. About 1 to 2 molar equivalents of the aromatization agent should be used.

The reaction is preferably performed by dissolving the product of the previous reaction in a solvent, such as trichlorobenzene or monochlorobenzene, and heating at a temperature of about 100° to about 170° C. When air or oxygen are used as the oxidant, it is preferable to add 1 to 5 wt % activated carbon. Lower temperatures require a longer reaction time but temperatures between 130° and 150° C. are preferred when air or oxygen is used as the aromatization agent. If 4-chlorophthalic or 4-bromophthalic anhydride is the desired product, higher temperatures may result in the loss of a chlorine or bromine atom, forming phthalic anhydride instead. The reaction can be performed under pressure. The final product has the following formula, where $R_1$ and $R_4$ are not halogen.

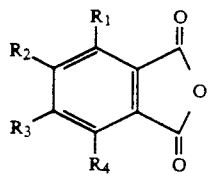

The preferred product is 4-chlorophthalic anhydride (4-CPAN).

The product can be isolated by titration of the activated carbon and removal of solvent by distribution. Alternatively the product may be isolated by recrystallization from the reaction solvent after filtration of the activated carbon. We have found that the product contains no hydrochloric or hydrobromic acids and only small amounts of phthalic anhydride. The phthalic anhydride can be distilled off or left in the reaction mixture if it does not react in subsequent reactions.

ALTERNATIVE AROMATIZATION PROCEDURE

While 4-FPAN can be made by following the hereinabove described procedures using fluoroprene as the conjugated diene, fluoroprene is an expensive starting material. The following alternative process can be used with the cycloadduct or with the product of the elimination reaction to form 4-FPAN, or other products, while avoiding the use of fluoroprene.

In this alternative reaction the product of the elimination reaction is reacted with a source of hydrofluoric acid in the presence of a source of a chlorine or bromine. Examples of sources of hydrogen fluoride include pyridinium poly(hydrogen fluoride), gaseous hydrogen fluoride, liquid hydrogen fluoride, triethylammonium tris (hydrogen fluoride), tetrahydrofuran poly(hydrogen fluoride), and diethyl ether poly(hydrogen fluoride). The preferred source of hydrogen fluoride is pyridinium poly(hydrogen fluoride) because it is an effective and reasonably safe reagent on the laboratory scale.

Examples of sources of chlorine and bromine include NBS, NCS, bromine and chlorine. The preferred bromine source is NBS on the laboratory scale because it is easily handled, inexpensive and works well.

The reaction can be performed with or without a solvent, but it is preferably performed in the absence of a solvent. Examples of suitable solvents that can be used include methylene chloride, diethylether, xylene, and toluene. In this reaction, one or both of $R_2$ or $R_3$ must be halogen. When the reactants are NBS, pyridinium poly (hydrogen fluoride) and

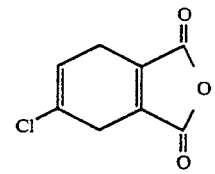

the reaction proceeds immediately at room temperature.

The major product is

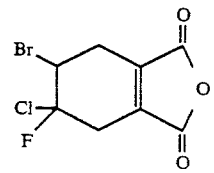

but some

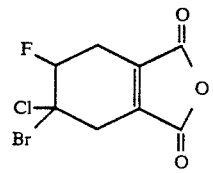

is also produced. The major product can be recovered by distillation or it may be reacted further without purification. After distillation and recovery of the major product it can be treated with an amine base, such as 1,8-diazabicyclco[5,4,0]undec-7-ene (DBU), at room temperature, which produces 4-FPAN and some 4-CPAN. 4-FPAN can be used as a dye intermediate.

Dimethyl 4-fluorophthalate can also be prepared according to the hereinabove described procedure using either fluoroprene or chloroprene as a dienophile. The trihalo intermediate can be treated with amine bases to effect elimination of hydrogen halides in a manner analogous to the anhydride reaction described above. Alternatively, the intermediate can be treated with hydroxide containing bases, such as sodium hydroxide, to yield, after neutralization, 4-fluorophthalic acid or 4-chlorophthalic acid. These acids can be converted to 4-fluorophthalic anhydride or 4-chlorophthalic anhydride by chemical or thermal cylization.

The following examples further illustrate this invention.

EXAMPLE 1

A 3-necked 50 mL flask was equipped with a pressure equalizing additional funnel, a thermocouple well with a thermocouple, a water cooled condensor and a magnetic stir bar. The flask was charged with 6.62 g (0.05 mol) of monochloromaleic anhydride contaminated with approximately 0.005 mol of dichloromaleic anhydride, 6.1 g of monochlorobenzene and 100 mg of phenothiazine. The contents of the flask were heated to 92° C. and 4.42 g (0.05 mol) of chloroprene was added over 15 to 30 minutes. HCl gas was observed evolving from the reactor. After 16 hours at 92° C., the solvent was removed in-vacuo and triturated with 10 mL of diethyl ether to yield 4.6 g (50% of theoretical) of 4-chloro-3,6-dihydrophthalic anhydride. High resolution mass spectrometry (MS) of the solid resulted in the following analysis: Calculated mass=183.99271; observed mass=183.9924. $^{13}C$ and $^1H$ nuclear magnetic resonance (NMR) spectra were consistent with the assigned structure.

EXAMPLE 2

A 3-necked 50 mL flask was equipped with a pressure equalizing additional funnel, a thermocouple well with thermocouple, a water cooled condenser and a magnetic stir bar. The flask was charged with 6.62 g (0.05 mol) of monochloromaleic anhydride contaminated with approximately 0.005 mol of dichloromaleic anhydride, 6.1 g of toluene and 100 mg of phenothiazine. The contents of the flask were heated to 80° C. and 4.42 g (0.05 mol) of chloroprene was added over 15 to 30 minutes. HCl gas was not observed evolving from the reactor. After 8 hours at 92° C., the solvent was removed in-vacuo at 20° C. 10.6 grams of a light oil was analyzed by $^1H$ NMR and shown to be a 4:1 molar ratio mixture of dichlorinated 1,2,3,6-tetrahydrophthalic anhydrides.

EXAMPLE 3

This example demonstrates that no solvent is required to carry out the cycloaddition and elimination reactions of this invention.

A 3-necked 50 mL flask was equipped with a pressure equalizing addition funnel, a thermocouple well with thermocouple, a water cooled condenser and a magnetic stir bar. The flask was charged with 13.2 g (0.10 mol) of a 90/10 GC area % mixture of monochloromaleic anhydride and dichloromaleic anhydride and 50 mg of phenothiazine. The contents of the flask were heated to 80 to 130° C. and 8.8 g (0.1 mol) of chloroprene was added over 15 to 30 minutes. HCl gas was observed evolving from the reactor. After 6 hours at 130° C. the contents of the flask were multiple distilled into two fractions resulting in the isolation of 12.08 g of 4-chloro-3,6-dihydrophthalic anhydride which was identified by $^{13}C$ $^1H$ NMR and MS.

EXAMPLE 4

This example shows that the entire sequence of cycloaddition, elimination and aromatization can be carried out in a single vessel with a good yield of 4-chlorophthalic anhydride.

A 3-necked 50 mL flask was equipped with a pressure equalizing addition funnel, a thermocouple well with thermocouple, a water cooled condenser and a magnetic stir bar. The flask was charged with 13.2 g (0.10 mol) of a 90/10 GC area % mixture of monochloromaleic anhydride and dichloromaleic anhydride and 100 mg of phenothiazine and 0.5 g of activated carbon. The contents of the flask were heated to 80 to 130° C. and 8.8 g (0.1 mol) of chloroprene was added over 15 to 30 minutes. HCl gas was observed evolving from the reactor. After 6 hours at 130° C. the contents of the flask were sparged with oxygen for 2 hours between 130° and 150° C., filtered hot, and multiple distilled into two fractions resulting in the isolation of 13.2 g (80% of theoretical) of 4-chlorophthalic anhydride.

EXAMPLE 5

This example shows the effect of omitting activated carbon from the reaction mixture.

A 3-necked 50 mL flask was equipped with a pressure equalizing addition funnel, a thermocouple well with thermocouple, a water cooled condenser and a magnetic stir bar. The flask was charged with 31.2 g (0.10 mol) of a 90/10 GC area % mixture of monochloromaleic anhydride and dichloromaleic anhydride and 100 mg of phenothiazine. The contents of the flask were heated to 80° to 130° C. and 8.8 g (0.1 mol) of chloroprene was added over 15 to 30 minutes. HCl gas was observed evolving from the reactor. Oxygen was sparged into the reaction mixture at 130° to 140° C. for 16 hours and the reaction was followed by GC. GC analysis indicated 6.54 g of 4-chlorophthalic anhydride.

EXAMPLE 6

This example demonstrates the importance of temperature in carrying out the aromatization reaction.

10 mg of 4-chloro-3,6-dihydrophthalic anhydride was dissolved in 0.25 mL of acetone-d6 and the solution placed in a 5 mm NMR tube and flushed with nitrogen. The tube was sealed and warmed in an air circulation oven at 210° C. for 2 hours and cooled to ambient temperature. The sample was analyzed by $^1H$ NMR and was shown to have converted to phthalic anhydride.

EXAMPLE 7

4-Chloro-3,6-dihydrophthalic anhydride

Chloroprene (13.6 g) and bromomaleic anhydride 14.6 g) were added together and the solution was heated to 50° C. for 11.5 hours. The reaction mixture was taken up in hot petroleum ether (bp 60° to 80° C.) and filtered. After cooling to room temperature, a solid was collected (6.2 g)- An additional 5 g of material remained in the mother liquors. The material consisted of a mixture of 4-chloro-3,6-dihydrophthalic anhydride, 4-chloro-1-bromo-1,2,3,6-tetrahydrophthalic anhydride and 4-chloro-2-bromo-1,2,3,6-tetrahydrophthalic anhydride.

EXAMPLE 8

Dimethyl 4-chloro-3,6-dihydrophthalate

Dimethyl acetylenedicarboxylate (6.3 g) and chloroprene (6.2 g) were heated at 50° C. for 25 hours. The reaction mixture was distilled under reduced pressure and the fraction boiling at 135° to 138° C. at 2.5 torr was collected. The thick oil weighed 4.6 g (100% yield based on unreacted dimethyl acetylenedicarboxylate).

EXAMPLE 9

5Bromo-4-chloro-4-fluoro-3,4,5,6-tetrahydrophthalic anhydride

Pyridinium poly(hydrogen fluoride) was added to a solid mixture of 4-chloro-3,6-dihydrophthalic anhydride (0.22 g) and N-bromosuccinimide (0.21 g) at room temperature. The reaction mixture was stirred for 3.25 hours and then carefully poured into a two phase system containing saturated sodium carbonate and methylene chloride. The methylene chloride layer was dried over magnesium sulfate and the solvent removed under reduced pressure. The residue was analyzed by NMR and GC-MS and contained 5-bromo -4-fluoro-3,4,5,6-tetrahydrophthalic anhydride as the major product along with some 4-fluorophthalic anhydride.

EXAMPLE 10

4,5-Dichloro-4-fluoro-3,4,5,6-tetrahydrophthalic anhydride 4-chloro-3,6-dihydrophthalic anhydride (0.63 g) and N-chlorosuccinimide (0.47 g) in methylene chloride (6.2 ml) was added to pyridinium poly(hydrogen fluoride) at room temperature. The reaction mixture was stirred for 2 hours and then carefully poured into a two phase system containing solid sodium carbonate and methylene chloride. The suspension was filtered, the methylene chloride layer was dried over magnesium sulfate and the solvent removed under reduced pressure.

EXAMPLE 11

Dimethyl-4,5-dichloro-4-fluoro-3,4,5,6-tetrahydrophthalate

Dimethyl 4-chloro-3,6-dihydrophthalate (1.1 g) and N-chlorosuccinimide (0.6 g) in methylene chloride (4.1 g) was added to pyridinium poly(hydrogen fluoride) (3.1 g) at room temperature. The reaction mixture was stirred at room temperature for 2 hours. The reaction mixture was carefully poured into methylene chloride containing solid sodium carbonate. The methylene chloride layer was filtered and dried with magnesium sulfate and the solvent removed under reduced pressure.

EXAMPLE 12

Dimethyl 5-bromo-4-chloro-4-fluoro-3,4,5,6-tetrahydrophthalate

Dimethyl 4-chloro-3,6-dihydrophthalate (0.19 g) and pyridinium poly(hydrogen fluoride) were mixed together at room temperature and N-bromosuccinimide was slowly added. The reaction mixture turned dark then light yellow. After stirring at room temperature for 3 hours, the reaction mixture was carefully poured into saturated sodium bicarbonate solution containing methylene chloride. The methylene chloride layer was dried with magnesium sulfate and the solvent removed under reduced pressure. NMR and GC-MS analysis of the reaction mixture revealed the major product to be the desired dimethyl 5-bromo-4-chloro-4-fluoro-3,4,5,6-tetrahydrophthalate along with some dimethyl 4-fluorophthalate.

EXAMPLE 13

5-Bromo-4-chloro-4-fluoro-3,4,5,6-tetrahydrophthalic anhydride

Pyridinium poly(hydrogen fluoride) was added to a solution of 4-chloro-3,6-dihydrophthalic anhydride (6.5 g) in methylene chloride (10.1 g) at room temperature. Bromine (3.1 g) was added. A violent reaction occurs. The solution was allowed to stand for 6 hours and then was poured into a two phase mixture of methylene chloride (30 ml) and solid sodium carbonate. The suspension was stirred for 10 minutes until bubbling stopped. The mixture was filtered and the methylene chloride removed under reduced pressure. The material was purified by a bulb to bulb distillation (140° C. air temperature and 2.8 torr) to give a yellowish solid, (3.74 g).

EXAMPLE 14

4-Fluorophthalic Anhydride

5-Bromo-4-chloro-4-fluoro-3,4,5,6-tetrahydrophthalic anhydride was reacted with 1,8-diazobicyclo[5,4,0]undec-7-ene (DBU) at room temperature in deuterochloroform for 15 minutes. Analysis by NMR indicated the presence of 4-fluorophthalic anhydride.

EXAMPLE 15

Dimethyl-4-fluorophthalate

Dimethyl-5-bromo-4-chloro-4-fluoro-3,4,5,6-tetrahydrophthalate was dissolved in deuterochloroform and DBU was added. Analysis by NMR showed the presence of dimethyl 4-fluorophthalate within 15 minutes at room temperature.

EXAMPLE 16

Dimethyl-4-fluorophthalate

Dimethyl 5-bromo-4-fluoro-3,4,5,6-tetrahydrophthalate was dissolved in methylene chloride and stirred over basic alumina for 4 hours. An aliquot was removed and the major product shown to be dimethyl 4-fluorophthalate by GC analysis.

EXAMPLE 17

Dimethyl-4-fluorophthalate

Dimethyl 4-chloro-3,6-dihydrophthalate (5.0 g) was added to pyridinium poly(hydrogen fluoride) (17.8 g). The solution was added to N-bromo-succinimide (3.9 g) and allowed to stir for 20 minutes. The reaction mixture was carefully poured onto a mixture of potassium carbonate (115 g) and ether (100 ml). Water was carefully added after the visible bubbling stopped. The two phases were separated and the aqueous layer washed with ether. The combined organic phases were dried over magnesium sulfate, filtered and then reduced in volume to about 100 ml under reduced pressure. DBU (5.0 g) was added. The reaction became warm. The reaction mixture was allowed to stand overnight. The reaction mixture was washed first with 10% aqueous hydrochloric acid followed by saturated potassium carbonate. The ether layer was dried over magnesium sulfate, filtered and the solvent removed under reduced pressure on a rotary evaporator under reduced pressure. The residue was purified by bulb to bulb distillation (100° to 105° C. air temperature, 1.5 torr) to give a colorless solid (3 g) which consisted of a 4:1 mixture of dimethyl 4-fluorophthalate and dimethyl 4-chlorophthalate.

EXAMPLE 18

4-Chloro-3,6-dihydrophthalic anhydride

Bromomaleic anhydride (18 g) was heated to 65° C. and crude chloroprene in toluene (50% solution, 34.6 g solution, 17.3 g chloroprene) was added. The solution was heated at reflux for 48 hours. The solvents and excess chloroprene were removed under reduced pressure on a rotary evaporator and the residue was purified by bulb to bulb distillation (125° to 130° C. air temperature, 2 torr) to give a whitish solid (16.6 g) which consisted of a mixture of 4-chloro-3,6-dihydrophthalic anhydride, 4-chloro-1-bromo-3,4,5,6-tetrahydrophthalic anhydride and 4-chloro-2-bromo-3,4,5,6-tetrahydrophthalic anhydride.

EXAMPLE 19

4-Fluorophthalic anhydride

Pyridine poly(hydrogen fluoride) (13.8 g) was added to a mixture of 4-chloro-3,6-dihydrophthalic anhydride, 4-chloro-1-bromo-1,2,3,6-tetrahydrophthalic anhydride and 4-chloro-2-bromo-1,2,3,6-tetrahydrophthalic anhydride (3.6 g). NBS (3.5 g) was added all at once to the reaction mixture. The reaction mixture was stirred until all solids dissolved. The reaction mixture was carefully poured onto a slurry of sodium carbonate (96 g), magnesium sulfate (23 g), and ether (100 ml). The ether was filtered, the solids washed with methylene chloride, and the combined organic phases dried over magnesium sulfate. The organic phase was filtered and DBU (10 g) was added. The reaction mixture was then washed with 10% aqueous hydrogen chloride, water, and then dried over magnesium sulfate. The solution was filtered and the solvent evaporated under reduced pressure. The residue was purified via bulb to bulb distillation (110° to 130° C., torr) to give an off-white solid (0.8 g) which consisted of a 3:2 mixture of 4-fluorophthalic anhydride and 4-chlorophthalic anhydride by GC analysis.

We claim:

1. A method of making 4-substituted phthalic anhydride comprising (a) reacting a halo substituted compound having the formula

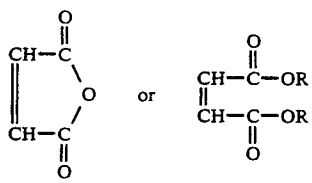

where R is H, alkyl to $C_{10}$, or aryl and X is Cl or Br, with a conjugated diene having the formula

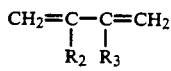

to form a first cycloadduct having the formula

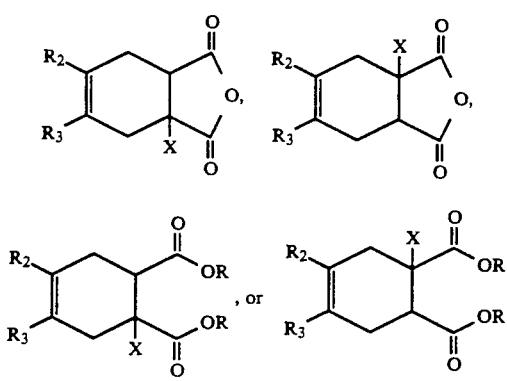

where $R_2$ is hydrogen or halo and $R_3$ is halo;

(B) heating said first cycloadduct to eliminate HX and produce a second cycloadduct having the formula

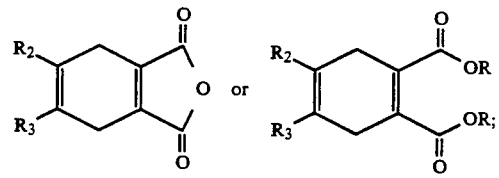

and (c) dehydrogenating said second cycloadduct to produce a 4-substituted phthalic anhydride having the formula

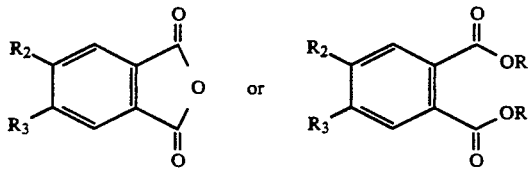

by forming a solution of said second cycloadduct and heating said solution to a temperature of about 100° to about 170° C. using an aromatization agent in the presence of an activated carbon catalyst.

2. A method according to claim 1 including the additional step of making said halo substituted compound by reacting maleic anhydride with chlorine or bromine.

3. A method according to claim 1 wherein said diene is chloroprene.

4. A method according to claim 1 wherein said diene is fluoroprene.

5. A method according to claim 1 wherein said diene is bromoprene.

6. A method according to claim 1 wherein X is Cl.

7. A method according to claim 1 wherein one of $R_2$ and $R_3$ is halogen and said second cycloadduct is reacted with a source of HF in the presence of a source of chlorine or bromine to produce a third cycloadduct having the formula

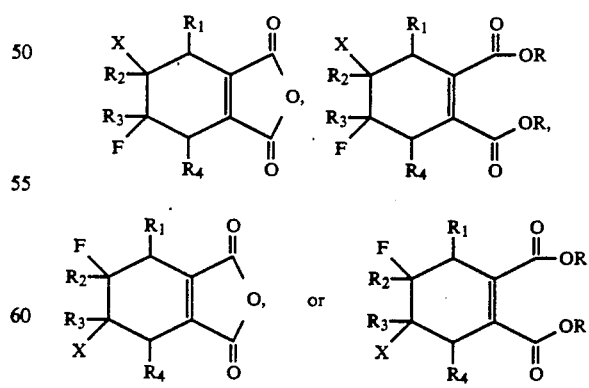

where X is Cl or Br, and said third cycloadduct is reacted with a tertiary amine.

8. A method according to claim 7 wherein said second cycloadduct is

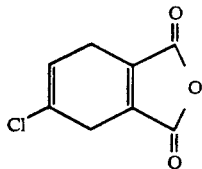

9. A method according to claim 7 wherein said source of HF is pyridinium poly(hydrogen fluoride).

10. A method according to claim 7 wherein said source of bromine is N-bromosuccinimide.

11. A method of making a 4-halophthalic anhydride comprising (A) reacting maleic anhydride with chlorine or bromine at a temperature of about 130° to about 170° C. to produce a halo substituted maleic anhydride having the formula

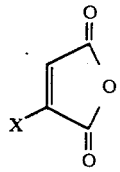

where X is Cl or Br;

(B) reacting said halo substituted maleic anhydride with chloroprene or fluoroprene at a temperature from about room temperature to about 120° C. to produce a first cycloadduct having the formula

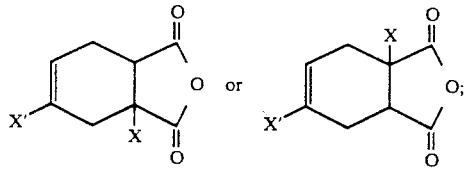

where X' is Cl or F;

(c) heating said first cycloadduct to a temperature of about 60° to about 170° C. to eliminate HX and form a second cycloadduct having the formula

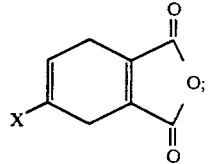

and (D) contacting a solution of said second cycloadduct heated to a temperature of about 100° to about 170° C. with activated carbon while blowing air therethrough.

12. A method according to claim 11 herein X is Cl.

13. A method according to claim 11 wherein in step (B) said halosubstituted maleic anhydride is reacted with chloroprene.

14. A method according to claim 11 wherein the reaction in step (A) is performed in the presence of AlCl$_3$.

15. A method of making a 4-halophthalic anhydride comprising (A) reacting maleic anhydride with chlorine or bromine at a temperature of about 130° to about 170° C. to produce a halo substituted maleic anhydride having the formula

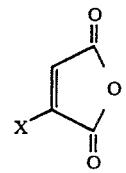

where X is Cl or Br;

(B) reacting said halo substituted maleic anhydride with chloroprene or fluoroprene at a temperature from about room temperature to about 120° C. to produce a first cycloadduct having the formula

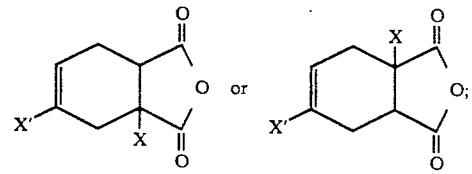

where X' is Cl or F;

(C) heating said first cycloadduct to a temperature of about 60° to about 170° C. to eliminate HX and form a second cycloadduct having the formula

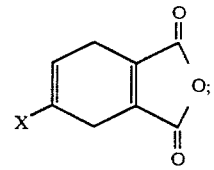

and (D) reacting said second cycloadduct with a source of HF in the presence of a source of chlorine or bromine to produce a third cycloadduct having the formula

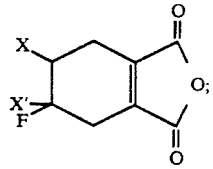

and (E) reacting said third cycloadduct with a tertiary amine to produce a 4-halophthalic anhydride.

16. A method according to claim 15 wherein X is Cl.

17. A method according to claim 14 wherein in step (B) said halo substituted maleic anhydride is reacted with chloroprene.